(12) United States Patent
Ziolo et al.

(10) Patent No.: US 10,010,357 B2
(45) Date of Patent: Jul. 3, 2018

(54) BONE FIXATION DEVICE

(71) Applicant: Zimmer Biomet Spine, Inc., Westminster, CO (US)

(72) Inventors: Tara Ziolo, Morris Plains, NJ (US); Rui Ferreira, Livingston, NJ (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

(21) Appl. No.: 14/254,198

(22) Filed: Apr. 16, 2014

(65) Prior Publication Data

US 2014/0228895 A1    Aug. 14, 2014

Related U.S. Application Data

(63) Continuation of application No. 13/088,873, filed on Apr. 18, 2011, now Pat. No. 8,828,064, which is a continuation of application No. 10/821,229, filed on Apr. 8, 2004, now Pat. No. 7,942,913.

(51) Int. Cl.
    *A61B 17/80*     (2006.01)
    *A61B 17/88*     (2006.01)
    *A61B 17/86*     (2006.01)

(52) U.S. Cl.
    CPC ...... *A61B 17/8047* (2013.01); *A61B 17/8615* (2013.01); *A61B 17/8685* (2013.01); *A61B 17/888* (2013.01); *A61B 17/861* (2013.01)

(58) Field of Classification Search
    CPC ...................................... A61B 17/80–17/8095
    USPC ........ 606/280–299, 300, 305, 319, 325–327, 606/86 B; 403/343, 362; 411/15, 349
See application file for complete search history.

(56) References Cited

U.S. PATENT DOCUMENTS

| | | | |
|---|---|---|---|
| 2,248,054 A | 7/1941 | Decker |
| 2,293,930 A | 8/1942 | Braendel |
| 2,580,821 A | 1/1952 | Nicola |
| 2,780,223 A | 2/1957 | Haggland |

(Continued)

FOREIGN PATENT DOCUMENTS

| EP | 1570796 A1 | 9/2005 |
|---|---|---|
| FR | 2844702 A1 | 3/2004 |
| WO | 2004/028334 A2 | 4/2004 |

OTHER PUBLICATIONS

"spherical". Merriam-Webster Online Dictionary [online], [retrieved on Nov. 16, 2006]. Retrieved from the Internet <URL: www.m-w.com. citedby examiner.

(Continued)

*Primary Examiner* — Jan Christopher Merene
*Assistant Examiner* — Steven Cotroneo
(74) *Attorney, Agent, or Firm* — Schwegman Lundberg & Woessner, P.A.

(57) ABSTRACT

A bone fixation apparatus is provided and includes a bone fixation plate having a fixation hole, a fastener shaft having a bone-anchoring portion and an upper portion defining an outer cam, and a C-shaped annular member having an outer surface, an inner surface defining an inner cam, and a gap formed through the entire annular member. The inner cam cooperates with the outer cam of the fastener shaft to move the annular member between an unexpanded position and an expanded position independent from movement of the fastener shaft relative to the bone fixation plate.

20 Claims, 9 Drawing Sheets

(56) References Cited

U.S. PATENT DOCUMENTS

| | | | |
|---|---|---|---|
| 3,515,418 A * | 6/1970 | Nielsen, Jr. | A61B 5/021 248/188.5 |
| 3,741,205 A | 6/1973 | Markolf et al. | |
| 4,279,249 A | 7/1981 | Vert et al. | |
| 4,388,921 A | 6/1983 | Sutter et al. | |
| 4,473,068 A | 9/1984 | Oh | |
| 4,484,570 A | 11/1984 | Sutter et al. | |
| 4,503,848 A | 3/1985 | Caspar et al. | |
| 4,655,203 A | 4/1987 | Tormala et al. | |
| 4,743,257 A | 5/1988 | Tormala et al. | |
| 4,790,703 A | 12/1988 | Wing | |
| 4,903,691 A | 2/1990 | Heinl | |
| 4,905,680 A | 3/1990 | Tunc | |
| 5,053,036 A | 10/1991 | Perren et al. | |
| 5,057,109 A | 10/1991 | Olerud et al. | |
| 5,080,665 A | 1/1992 | Jarrett et al. | |
| 5,108,399 A | 4/1992 | Eitenmuller et al. | |
| 5,129,903 A | 7/1992 | Luhr et al. | |
| 5,139,498 A | 8/1992 | Astudillo Ley | |
| 5,147,360 A | 9/1992 | Dubousset et al. | |
| 5,158,409 A | 10/1992 | Ishida et al. | |
| 5,180,381 A | 1/1993 | Aust et al. | |
| 5,290,281 A | 3/1994 | Tschakaloff | |
| 5,346,492 A | 9/1994 | Morgan | |
| 5,364,399 A | 11/1994 | Lowery et al. | |
| 5,376,102 A | 12/1994 | Jarrett et al. | |
| 5,423,826 A | 6/1995 | Coates et al. | |
| 5,468,242 A | 11/1995 | Reisberg | |
| 5,520,690 A | 5/1996 | Errico et al. | |
| 5,531,746 A | 7/1996 | Errico et al. | |
| 5,569,250 A | 10/1996 | Sarver et al. | |
| 5,578,034 A | 11/1996 | Estes | |
| 5,578,046 A | 11/1996 | Liu et al. | |
| 5,601,553 A | 2/1997 | Trebing et al. | |
| 5,607,426 A | 3/1997 | Ralph et al. | |
| 5,607,427 A | 3/1997 | Tschakaloff | |
| 5,607,428 A | 3/1997 | Lin | |
| 5,676,666 A | 10/1997 | Oxland et al. | |
| 5,681,311 A | 10/1997 | Foley et al. | |
| 5,690,631 A | 11/1997 | Duncan et al. | |
| 5,702,396 A | 12/1997 | Hoenig et al. | |
| 5,704,936 A | 1/1998 | Mazel et al. | |
| 5,707,372 A | 1/1998 | Errico et al. | |
| 5,709,686 A | 1/1998 | Talos et al. | |
| 5,713,898 A | 2/1998 | Stucker et al. | |
| 5,713,900 A | 2/1998 | Benzel et al. | |
| 5,718,705 A | 2/1998 | Sammarco | |
| 5,735,853 A | 4/1998 | Olerud et al. | |
| 5,766,176 A | 6/1998 | Duncan | |
| 5,797,914 A | 8/1998 | Leibinger et al. | |
| 5,800,433 A | 9/1998 | Benzel et al. | |
| 5,814,048 A | 9/1998 | Morgan | |
| 5,843,082 A | 12/1998 | Yuan et al. | |
| 5,868,746 A | 2/1999 | Sarver et al. | |
| 5,876,402 A | 3/1999 | Errico et al. | |
| 5,904,683 A | 5/1999 | Pohndorf et al. | |
| 5,925,048 A | 7/1999 | Ahmad et al. | |
| 5,954,722 A | 9/1999 | Bono | |
| 5,961,524 A | 10/1999 | Crombie | |
| 5,980,540 A | 11/1999 | Bruce | |
| 6,001,101 A | 12/1999 | Augagneur et al. | |
| 6,019,763 A | 2/2000 | Nakamura et al. | |
| 6,036,693 A | 3/2000 | Yuan et al. | |
| 6,039,740 A | 3/2000 | Olerud et al. | |
| 6,090,111 A | 7/2000 | Nichols | |
| 6,117,173 A | 9/2000 | Taddia et al. | |
| 6,129,730 A | 10/2000 | Bono et al. | |
| 6,147,135 A | 11/2000 | Yuan et al. | |
| 6,152,927 A | 11/2000 | Farris et al. | |
| 6,179,839 B1 | 1/2001 | Weiss et al. | |
| 6,193,721 B1 | 2/2001 | Michelson | |
| 6,206,881 B1 | 3/2001 | Frigg et al. | |
| 6,206,883 B1 | 3/2001 | Tunc | |
| 6,214,008 B1 | 4/2001 | Illi et al. | |
| 6,221,075 B1 | 4/2001 | Tormala et al. | |
| 6,228,085 B1 | 5/2001 | Theken et al. | |
| 6,235,033 B1 | 5/2001 | Brace et al. | |
| 6,241,771 B1 | 6/2001 | Gresser et al. | |
| 6,258,089 B1 | 7/2001 | Campbell et al. | |
| 6,261,291 B1 | 7/2001 | Talaber et al. | |
| 6,273,899 B1 | 8/2001 | Kramer | |
| 6,290,703 B1 | 9/2001 | Ganem | |
| 6,294,187 B1 | 9/2001 | Boyce et al. | |
| D449,692 S | 10/2001 | Michelson | |
| 6,306,140 B1 | 10/2001 | Siddiqui | |
| 6,322,562 B1 | 11/2001 | Wolter | |
| 6,331,179 B1 | 12/2001 | Freid et al. | |
| 6,342,055 B1 | 1/2002 | Eisermann et al. | |
| 6,361,537 B1 | 3/2002 | Anderson | |
| 6,383,186 B1 | 5/2002 | Michelson | |
| 6,398,783 B1 | 6/2002 | Michelson | |
| 6,402,756 B1 | 6/2002 | Ralph et al. | |
| 6,402,759 B1 | 6/2002 | Strong et al. | |
| 6,413,259 B1 | 7/2002 | Lyons et al. | |
| 6,416,528 B1 | 7/2002 | Michelson | |
| 6,423,068 B1 | 7/2002 | Reisberg et al. | |
| 6,428,542 B1 | 8/2002 | Michelson | |
| 6,440,135 B2 | 8/2002 | Orbay et al. | |
| 6,440,136 B1 | 8/2002 | Gambale et al. | |
| 6,454,769 B2 | 9/2002 | Wagner et al. | |
| 6,458,133 B1 | 10/2002 | Lin | |
| 6,503,250 B2 | 1/2003 | Paul | |
| 6,547,790 B2 | 4/2003 | Harkey, III et al. | |
| 6,585,769 B1 | 7/2003 | Muhanna et al. | |
| 6,595,993 B2 | 7/2003 | Donno et al. | |
| 6,599,290 B2 | 7/2003 | Bailey et al. | |
| 6,620,163 B1 | 9/2003 | Michelson | |
| 6,645,208 B2 | 11/2003 | Apfelbaum et al. | |
| 6,669,701 B2 | 12/2003 | Steiner et al. | |
| 6,689,134 B2 | 2/2004 | Ralph et al. | |
| 6,702,817 B2 | 3/2004 | Beger et al. | |
| 6,709,686 B1 | 3/2004 | Matthew | |
| 6,719,759 B2 | 4/2004 | Wagner et al. | |
| 6,730,091 B1 | 5/2004 | Pfefferle et al. | |
| 6,761,719 B2 | 7/2004 | Justis et al. | |
| 6,767,351 B2 | 7/2004 | Orbay et al. | |
| 6,786,909 B1 | 9/2004 | Dransfeld et al. | |
| 6,893,444 B2 | 5/2005 | Orbay | |
| 6,916,320 B2 | 7/2005 | Michelson | |
| 7,942,913 B2 | 5/2011 | Ziolo et al. | |
| 8,172,885 B2 | 5/2012 | Songer et al. | |
| 2001/0012940 A1 | 8/2001 | Tunc | |
| 2001/0014807 A1 | 8/2001 | Wagner et al. | |
| 2002/0045896 A1 | 4/2002 | Michelson | |
| 2002/0058939 A1 | 5/2002 | Wagner et al. | |
| 2002/0065517 A1 | 5/2002 | Paul | |
| 2002/0077630 A1 | 6/2002 | Lin | |
| 2002/0120268 A1 | 8/2002 | Berger | |
| 2002/0120273 A1 | 8/2002 | Needham et al. | |
| 2002/0183755 A1 | 12/2002 | Michelson | |
| 2003/0018335 A1 | 1/2003 | Michelson | |
| 2003/0078583 A1 | 4/2003 | Biedermann et al. | |
| 2003/0105462 A1 | 6/2003 | Haider | |
| 2003/0153919 A1 | 8/2003 | Harris | |
| 2003/0225409 A1 | 12/2003 | Freid et al. | |
| 2004/0039387 A1 | 2/2004 | Gause et al. | |
| 2004/0044345 A1 | 3/2004 | DeMoss et al. | |
| 2004/0068319 A1 | 4/2004 | Cordaro | |
| 2004/0073218 A1 | 4/2004 | Dahners | |
| 2004/0127896 A1 * | 7/2004 | Lombardo et al. | 606/61 |
| 2004/0127899 A1 * | 7/2004 | Konieczynski | A61B 17/7059 606/281 |
| 2004/0153092 A1 | 8/2004 | Beger et al. | |
| 2004/0181228 A1 | 9/2004 | Wagner et al. | |
| 2004/0236332 A1 | 11/2004 | Frigg | |
| 2004/0260291 A1 | 12/2004 | Jensen | |
| 2005/0004574 A1 | 1/2005 | Muckter | |
| 2005/0049593 A1 * | 3/2005 | Duong | A61B 17/8047 606/287 |

(56) References Cited

U.S. PATENT DOCUMENTS

2005/0143742 A1    6/2005  Porcher
2005/0184265 A1    8/2005  Aoki et al.
2007/0123879 A1*   5/2007  Songer ............... A61B 17/8033
                                                            606/288

OTHER PUBLICATIONS

"kink". Merriam-Webster Online Dictionary [online], [retrieved on Nov. 16, 2006]. Retrieved from the Internet <URL: www.m-w.com. cited by examiner.

Non-Final Office Action for U.S. Appl. No. 13/088,873, dated May 8, 2013.

Final Office Action for U.S. Appl. No. 13/088,873, dated Oct. 21, 2013.

Advisory Action for U.S. Appl. No. 13/088,873, dated Jan. 28, 2014.

Non-Final Office Action for U.S. Appl. No. 13/088,873, dated Nov. 1, 2012.

\* cited by examiner

BONE FIXATION DEVICE

CROSS-REFERENCE TO RELATED APPLICATIONS

This application is a continuation of U.S. patent application Ser. No. 13/088,873 filed on Apr. 18, 2011, which is a continuation of U.S. patent application Ser. No. 10/821,229 filed on Apr. 8, 2004 (now U.S. Pat. No. 7,942,913). The entire disclosures of the above applications are incorporated herein by reference.

INTRODUCTION

In certain orthopedic surgical procedures, it is necessary to secure multiple bones or bone portions relative to each other. For example, in spinal surgeries, the fusion of two or more vertebrae bodies is required to secure a portion of the spinal column in a desired position. This need may be the result of physical trauma from fractures or dislocations, degenerative diseases, or tumors.

One such spinal fixation procedure involves the attachment of a prosthesis or plate to the anterior side of the cervical portion of the spine. The procedure requires anteriorly accessing the spine and securing a prosthetic plate to the one or more cervical vertebrae. This allows fusion of the one or more cervical vertebrae in a particular orientation so to facilitate healing or to repair a condition of the patient.

Various fusion plates and plating systems are known for anteriorly fusing the cervical spine. Such plates and plating systems must meet several requirements that often are in conflict. For example, the requirements associated with spinal stability and system reliability over an extended period of use often conflict with the requirements of an easy to use implant. Strength requirements for a fusion plate tend to make the plate bulky and adversely effect intra-operative and postoperative viewing of the associate area of the spine. Additionally, it is desirable that the affected region of the cervical spine be easily viewed using MRI or x-ray procedures to verify that the desired fusion of the cervical spine is complete and/or that the alignment of the cervical vertebrae is proper.

Plating systems are also required to ensure that bone screws do not loosen over time or back out from the plate, further complicating the design of anterior plating systems. It is further desirable to ensure that the bone screws placed into the vertebrae through the plating system do not loosen or back out from the plate without requiring additional surgical steps. Furthermore, locking mechanisms should adequately permit the removal of an associated bone screw when required, and allow sufficient angular freedom for bone screws relative to a plate.

It remains desirable in the pertinent art to provide an improved anterior cervical plating system that addresses all the requirements discussed above.

SUMMARY

A bone fixation apparatus is provided and includes a bone fixation plate having a fixation hole, a fastener shaft having a bone-anchoring portion and an upper portion defining an outer cam, and a C-shaped annular member having an outer surface, an inner surface defining an inner cam, and a gap formed through the entire annular member. The inner cam cooperates with the outer cam of the fastener shaft to move the annular member between an unexpanded position and an expanded position independent from movement of the fastener shaft relative to the bone fixation plate.

In another configuration, a bone fixation apparatus is provided and includes a bone fixation plate having a fixation hole, a fastener shaft having a longitudinal axis extending between a first end and a second end thereof, and a circumferential groove formed in the fastener shaft and having at least one cam surface. The bone fixation apparatus additionally includes an annular member having an inner surface cooperating with the at least one cam surface to radially expand the annular member from an unexpanded position to an expanded position when the fastener shaft is in a fixed position relative to the bone fixation plate. The annular member includes separated ends defining a gap therebetween, whereby the gap is formed through the entire annular member.

In another configuration, a bone fixation apparatus is provided and includes a bone fixation plate having a fixation hole, a fastener shaft having a longitudinal axis extending between a first end and a second end thereof, and a circumferential groove formed in the fastener shaft and having at least one cam surface. The bone fixation apparatus additionally includes an annular member having an inner surface cooperating with the at least one cam surface to selectively expand the annular member from an unexpanded position to an expanded position independent of movement of the fastener shaft relative to the bone fixation plate. The annular member includes separated ends defining a gap therebetween, whereby the gap is formed through the entire annular member.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses.

Figure 1:
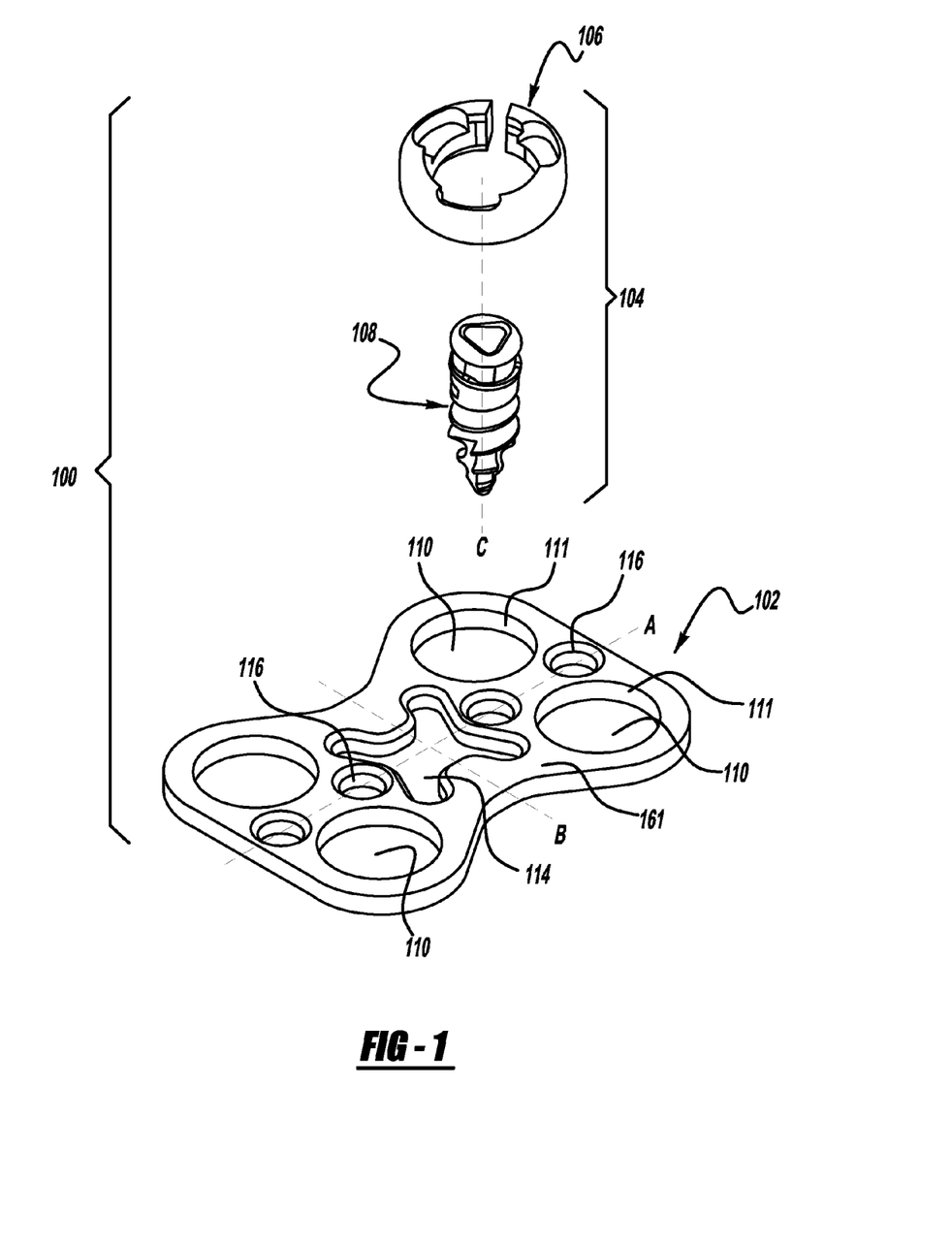
FIG. 1 is an exploded view of a fixation apparatus according to the present teachings.
Figure 2A:
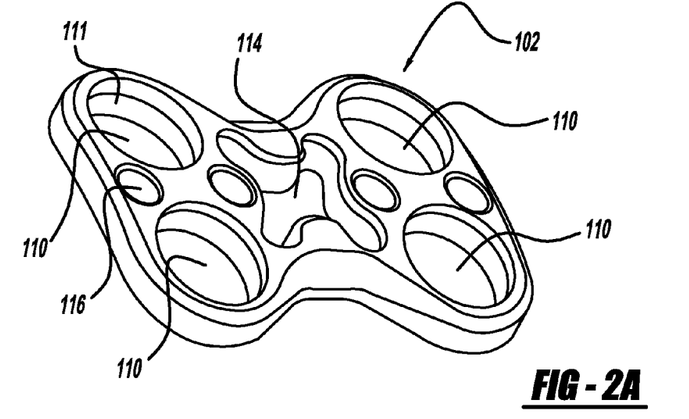
FIG. 2a is an isometric view of a fixation plate for connecting two bone portions according to the present teachings.
Figure 2B:
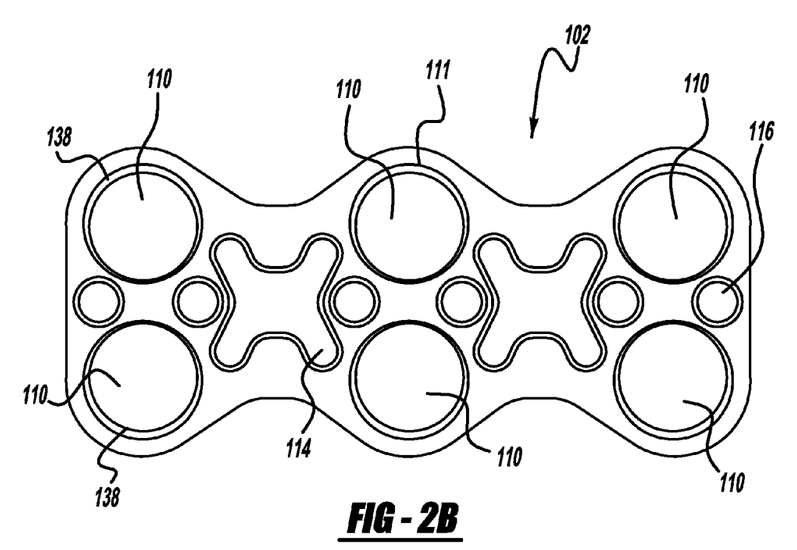
FIG. 2b is a top view of a fixation plate for connecting three bone portions according to the present teachings.
Figure 2C:
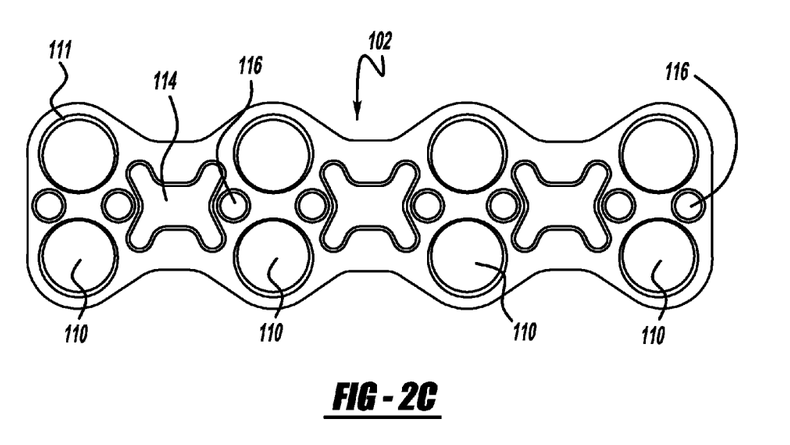
FIG. 2c is a top view of a fixation plate for connecting four bone portions according to the present teachings.
Figure 2D:
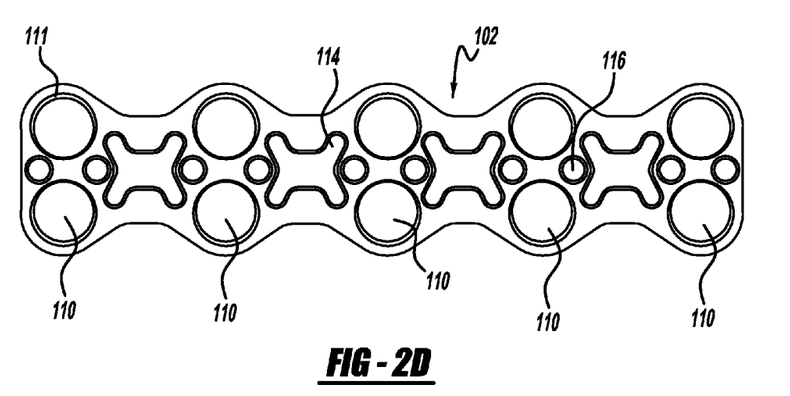
FIG. 2d is a top view of a fixation plate for connecting five bone portions according to the present teachings.

FIG. 1 illustrates an exploded view of a bone fixation apparatus 100 according to the present teachings. The bone fixation apparatus 100 generally includes a bone fixation plate 102 and a modular bone fixation fastener 104. The bone fixation fastener 104 includes an expandable head member 106 and a shaft member 108 having a shaft axis "C". The bone fixation plate 102 includes one or more fixation holes 110 through which the bone fixation fastener 104 is inserted to be affixed to a bone portion.

Figure 16:
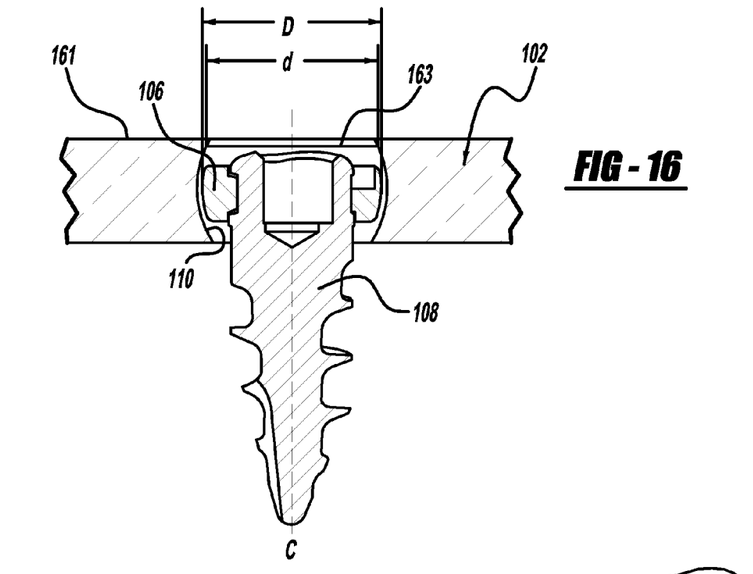
FIG. 16 is sectional view of a detail of a bone fixation apparatus according to the present teachings.
Figure 17:
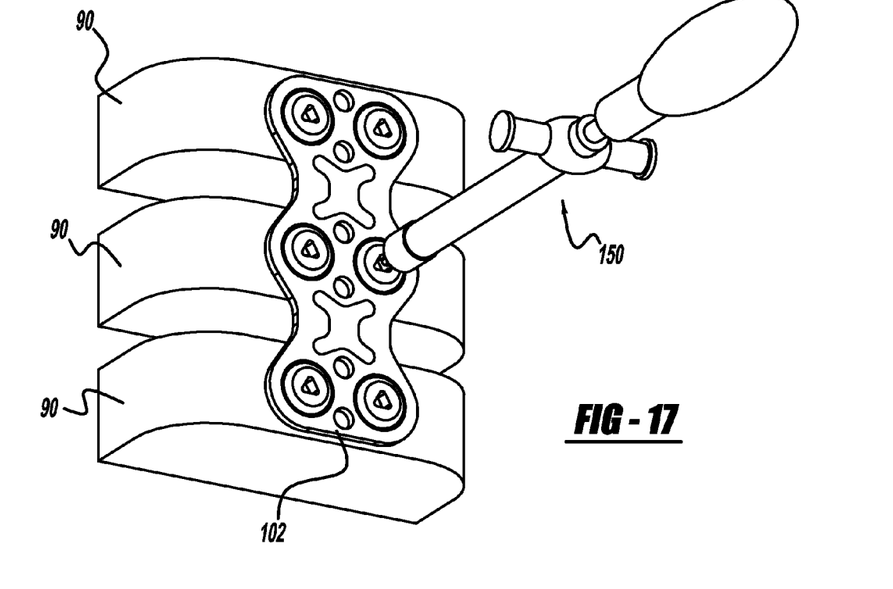
FIG. 17 is an environmental view of a bone fixation system according to the present teachings shown with a tool for inserting and removing the bone fixation fasteners.

FIGS. 2a to 2d illustrate examples of fixation plates 102 adapted for fixing together two to five bone portions 90, respectively, such as, for example, the vertebral bodies shown in FIG. 16. In the exemplary fixation plates 102 of FIGS. 2a-2d, the fixation holes 110 are arranged in pairs, two for each bone portion 90. Other arrangements are also within the scope of the present teachings. For example, one fixation hole 110 for each bone portion 90 may be provided, or more than two fixation holes 110 for each bone portion 90 may be provided. Each fixation hole 110 defines an inner surface 111, which may be spherical.

The fixation plate 102 can be shaped to conform to the bone portions 90 and have a curvature in one or two directions defined by a longitudinal axis "A" and a transverse axis "B", as shown in FIG. 1. It will be appreciated that the axes A and B, shown as orthogonal in FIG. 1, need not be so limited. Additionally, the fixation plate 102 can have different shapes and it can also be planar.

The fixation plate 102 can include a viewing window 114 to help monitor the location of any graft used in the fixation procedure and the progress of fusion in post-operative X-rays and MRI scans of the bone portions 90. The viewing window 114 can be defined between the sets of fixation holes 110 corresponding to contiguous bone portions or vertebral bodies 90, as shown in FIGS. 2a-2d. Additionally, the fixation plate 102 can include one or more anchoring holes 116 for pre-fixation anchoring or alignment using standard fasteners, such as tacks or screws or just the shaft member 108 of the fixation fastener 104.

Figure 3:
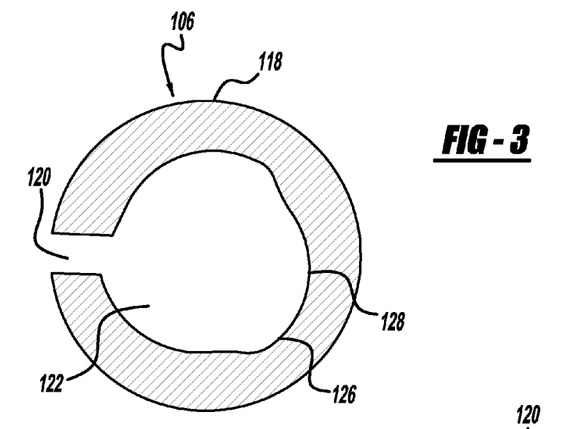
FIG. 3 is sectional view of a head member according to the present teachings.
Figure 4:
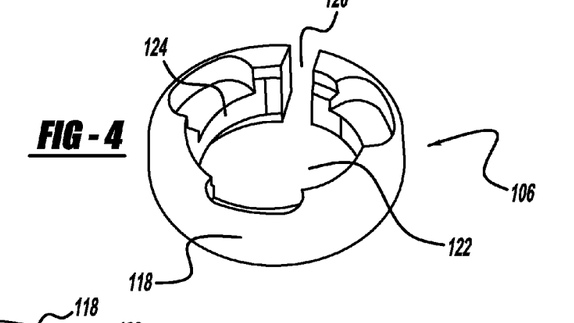
FIG. 4 is an isometric view of a head member according to the present teachings.
Figure 5:
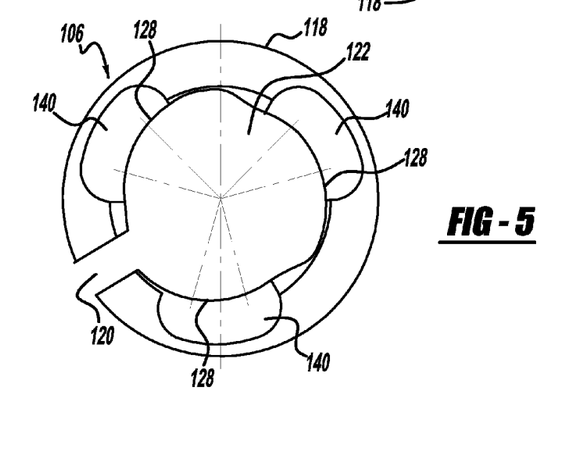
FIG. 5 is top view of a head member according to the present teachings.

Referring to FIGS. 3-5, the expandable head member 106 is bounded by an open curved surface 118 defining a gap 120 and a central opening 122. The central opening 122 has an inner surface 124, and is adapted to receive the shaft member 108. The gap 120 increases the resiliency of the head member 106, such that head member 106 can expand from a relaxed position in which no pressure is exerted to the inner surface 124, to a pressurized position in which pressure is exerted on the inner surface 124 causing the gap 120 to widen. The inner surface 124 of the head member 106 defines an inner head cam 126 with one or more lobes 128. Each lobe 128 of the inner head cam 126 can be constructed, for example, by offsetting a radius of a segment of the inner surface 124 by a certain radial distance and then connecting the offset regions with variable radius curves.

Figure 6:
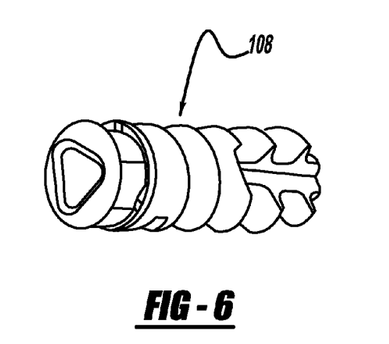
FIG. 6 is an isometric view of a shaft member according to the present teachings.
Figure 7:
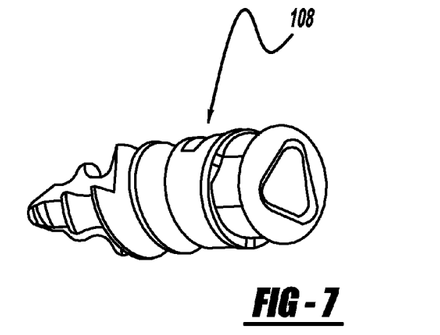
FIG. 7 is an isometric view of another shaft member according to the present teachings.
Figure 8:
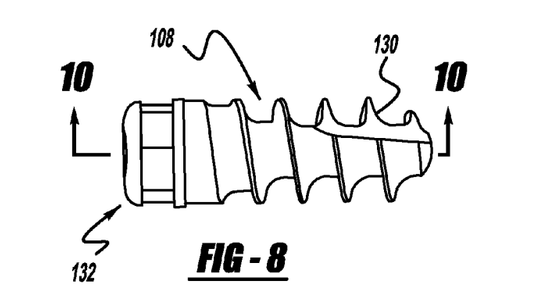
FIG. 8 is a side view of the shaft member of FIG. 6.
Figure 9:
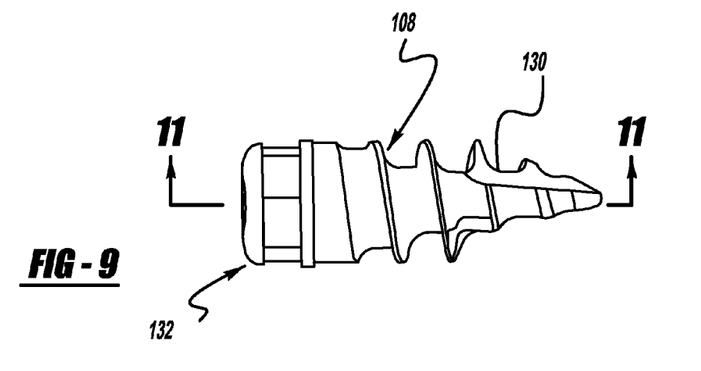
FIG. 9 is a side view of the shaft member of FIG. 7.
Figures 10, 11:
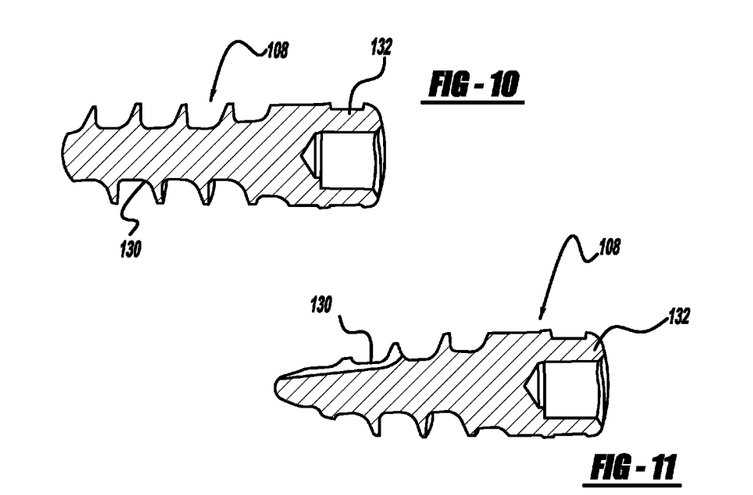
FIG. 10 is a longitudinal sectional view of the shaft member of FIG. 8 taken along line 10-10.
FIG. 11 is a longitudinal sectional view of the shaft member of FIG. 9 taken along line 11-11.
Figure 12:
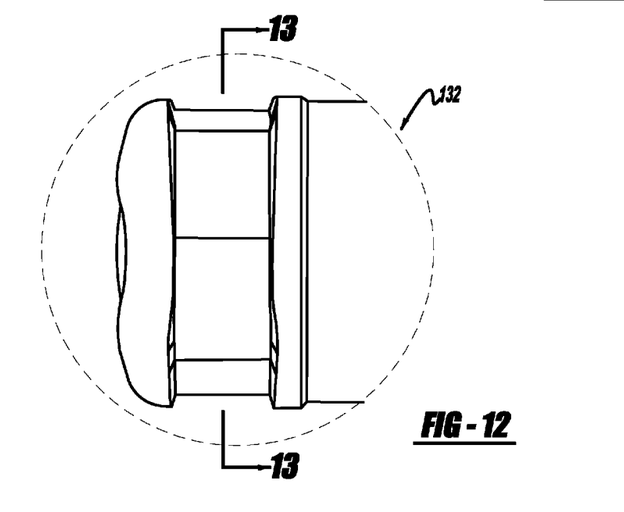
FIG. 12 is an enlarged view of Detail D of FIGS. 8 and 9.
Figure 13:
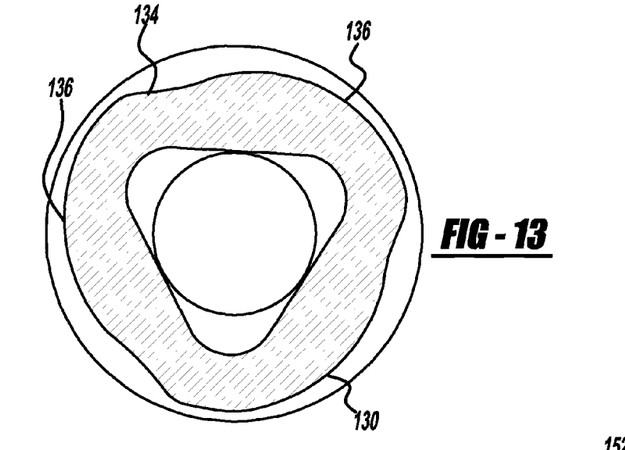
FIG. 13 is a sectional view of the Detail D of FIG. 12 along the axis 13-13.
Figure 14:
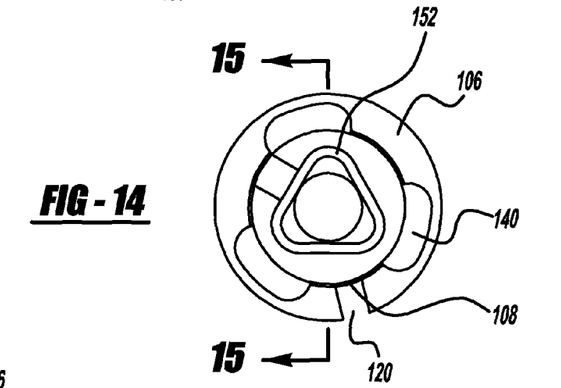
FIG. 14 is a top view of a bone fixation fastener according to the present teachings.
Figure 15:
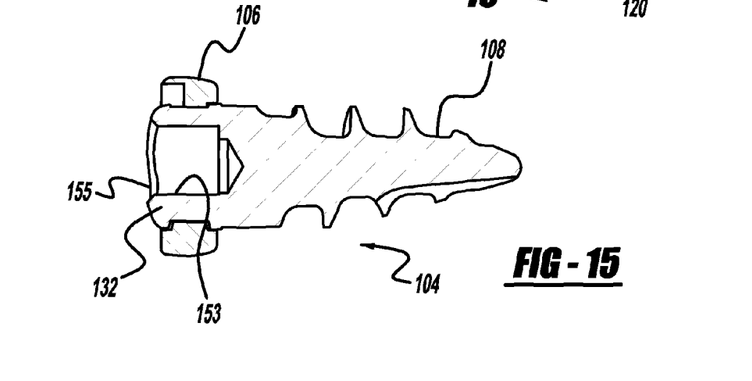
FIG. 15 is a sectional view of the bone fixation fastener of FIG. 14 along axis 15-15.

FIGS. 6-13 illustrate shaft members 108 according to the present teachings. In particular, FIGS. 7, 9 and 11 depict views of a self-drilling shaft member 108, while FIGS. 6, 8 and 10 depict views of a self-tapping shaft member 108. The shaft member 108 includes an insertion portion 130 having threads respectively adapted for self-drilling or self-tapping, and a distal portion 132 adapted to be retained by the head member 106. A magnified view of the distal portion 132 is illustrated as Detail D in FIG. 12. A sectional view of the distal portion 132 is shown in FIG. 13. The distal portion 132 defines a outer shaft cam 134 that has one or more lobes 136 adapted to mate with the lobes 128 of the inner head cam 126 while the head member 106 is in the relaxed position. In the relaxed position, the fixation fastener 104 can rotate freely and be seated in the fixation plate 102 at various angles relative to the plate 102.

When the head member 106 seats in the fixation hole 110 in the relaxed or unexpanded position, no pressure is exerted by the head member 106 to the inner surface 111 of the hole 110. The curved surface 118 of the head member 106 mates with the inner surface 111 of the fixation hole 110, such that the head member 106 can rotate freely relative to the inner surface 111 of the fixation hole 110 in the relaxed position. In the pressurized or expanded position, the expanded head member 106 is expanded toward the inner surface 111 of the hole 110.

Referring to FIG. 16, the head member 106 has a maximum diameter "D" which, in the unexpanded position of the head member 106, is smaller than an upper diameter "d" of the fixation hole 110 of the fixation plate, such that the head member 106 can be inserted through the fixation hole 110. The upper diameter d of the fixation hole is defined in a plane generally parallel to an upper surface 161 of the fixation plate. In the expanded position, the maximum diameter D is bigger than the upper diameter d of the fixation hole 110, preventing the head member 106 from backing out of the fixation hole 110 at the upper surface of the fixation plate.

In one application, the expanded diameter of the head member 106 is sufficiently large to press against the fixation hole 110. In this particular application, the expanded head member 106 not only prevents the head member 106 from backing out of the fixation hole 110, but also arrests relative movement of the plate 102 and the fastener 108. This relationship is referred to as a "constrained relationship".

In another application, the expanded diameter of the head member 106 remains sufficiently large to prevent the head member 106 from backing out of the fixation hole, but is not so large to preclude movement between the fastener 108 and the plate 102. In this regard, the head member 106 is permitted to articulate relative to the fixation hole 110 and thereby the fastener 108 may articulate relative to the plate 102. This relationship is referred to as a "semi-constrained relationship".

In certain applications, the head member 106 and fastener 108 may be cooperatively configured to alternatively provide both a constrained mode of operation and a semi-constrained mode of operation. In this regard, the lobes 128 of the head member 106 may cooperate with the lobes 136 of the fastener 108 to provide dual modes of operation. Explaining further, the head member 106 may be rotated from a relaxed or unexpanded state through a first rotation relative to the fastener 108 to expand the head member 106 to a first expanded diameter and further rotated through a second rotation relative to the fastener 108 to expand the head member 106 to a larger second expanded diameter. Similarly, the head member 106 may be rotated in a first direction relative to the fastener (e.g., clockwise or counterclockwise) to expand the head member 106 to the smaller first expanded diameter and further rotated in an opposite second direction to expand the head member 106 to the larger second expanded diameter.

In operation, the fixation plate 102 may be temporarily attached to the bone portions 90 with shaft members 108 or other fasteners through the anchoring holes 116. Each fixation fastener 104 is assembled by aligning the head member 106 with the shaft member 108 and placing the head member 106 over the shaft member 108. Each fixation fastener 104 seats on a countersunk portion 138 of the fixation hole 110 such that it can freely rotate, allowing the shaft member 106 to be placed in a desired orientation and be drilled or tapped into the bone portion 90. Once the shaft member 108 is anchored in the bone portion 90, the head member 106 can be rotated relative to the shaft member 108, such that the inner head cam 126 rotates out of alignment relative to the outer shaft cam 134 of the shaft member 108, causing the head member 106 to expand, thereby locking the fixation fastener 104 to the fixation plate 102 with compression forces therebetween.

Referring to FIGS. 14, and 17-19, the head member 106 can include slots or other engagement formations 140 for engaging the head member 106 with a first driver 158 to rotate the head cam 126 past the shaft cam 134 and cause the head member 106 to expand against the fixation hole 110, thereby locking the fixation fastener 104. The same driver 158 can be used to rotate the head member 106 in the opposite direction bringing the head and shaft cams 126 and 134 in lobe alignment to unlock the fixation fastener 104. The shaft member 108 can also have internal threads or other engagement formations 155 defined in an aperture 153 of the distal end 132, such that the shaft member 108 can be fastened to and unfastened from the bone 90 with a second driver 156 that has external threads 160 shaped to be inserted in the aperture 153 and engage the internal threads 155.

Figures 18, 19:
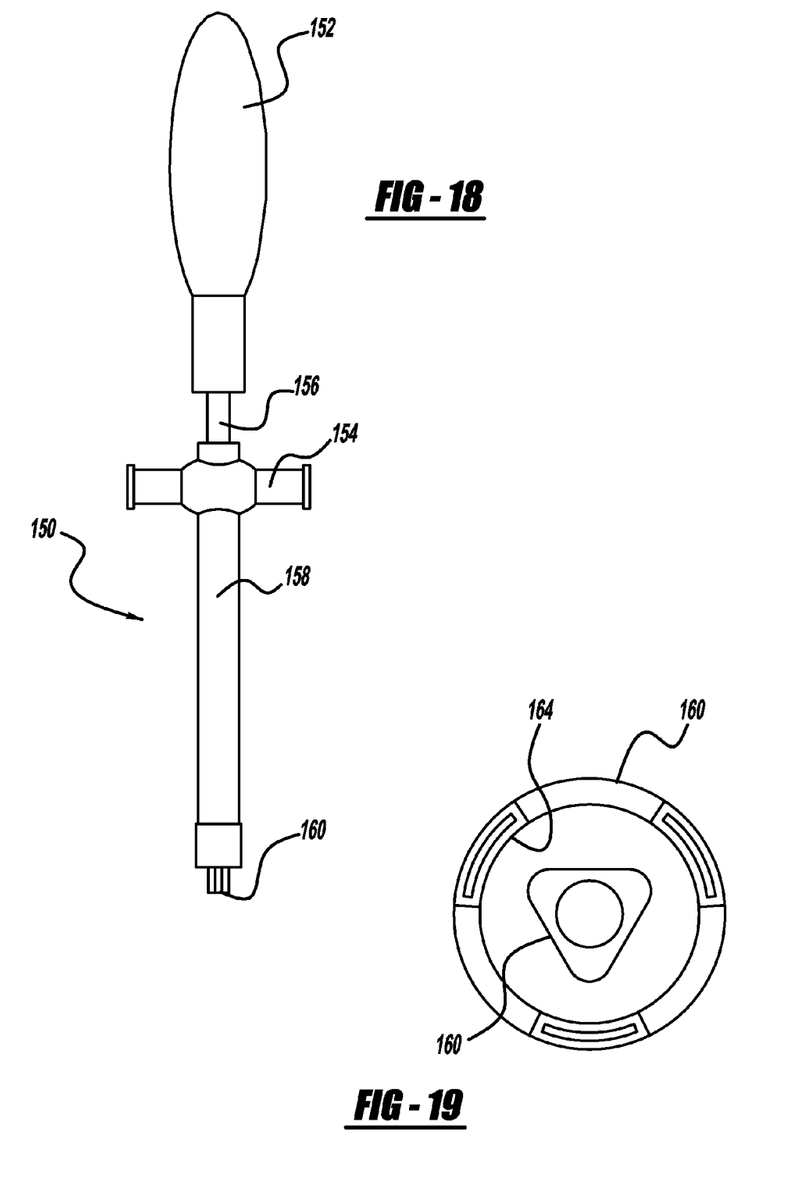
FIG. 18 is an enlarged view of the tool shown in FIG. 17.
FIG. 19 is a plan view of the tip of the tool shown in FIG. 18.

Referring to FIGS. 18 and 19, the first and second drivers 158 and 156 can be separate tools or can be combined in one tool 150 as follows. The first driver 158 is attached to a torque handle 154, and is hollow defining a bore 164. The second driver 156 is attached to a second handle 152 and passes through the bore 164. To insert the fixation fastener 104, the second driver 156 engages the internal threads 155 of the aperture 153 of the shaft member 108. The second handle 152 is rotated clockwise until the fixation fastener 104 is completely inserted into the bone portion 90 and the head member 106 is level with the fixation plate 102. The torque handle 154 is then rotated clockwise while the first driver 158 engages the slots 140 of the head member 106, causing the head member 106 to expand and lock the fixation fastener 104. To remove the fixation fastener 104, the reverse procedure is followed. The fixation fastener 104 is first unlocked by rotating the torque handle 154 counterclockwise to re-align the head cam 126 with the shaft cam 134 and return the head member to its unexpanded state, thereby loosening the fixation fastener 104 from the fixation plate 102. The second handle 152 is then rotated counterclockwise to remove the shaft member 108 from the bone 90.

It will be appreciated that the fixation apparatus 100 provides quick fixation and/or removal of the plate 102 to the bone portions 90 for bone repairs, while preventing the fastener 104 from backing out of the bone portions 90 after fixation. Furthermore, the fastener 104 can be readily oriented in a plurality of angles relative to the plate 102.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A bone fixation apparatus comprising:
a bone fixation plate having a fixation hole including an inner surface that is longitudinally curved relative to a hole longitudinal axis;
a fastener shaft having a bone-anchoring portion and an upper portion defining an outer circumferential cam; and
a C-shaped annular member having an outer surface that is longitudinally curved relative to the hole longitudinal axis, a lobed inner surface defining an inner circumferential cam, and a gap formed through the entire annular member, the inner circumferential cam cooperating with the outer circumferential cam of the fastener shaft to move the annular member between an unexpanded position and an expanded position independent from movement of the fastener shaft relative to the bone fixation plate;
wherein the inner surface and the outer surface engage to allow orientation of the fastener shaft at various angles relative to the hole longitudinal axis of the fixation hole of the bone fixation plate.

2. The bone fixation apparatus of claim 1, wherein the inner circumferential cam and the outer circumferential cam are configured to provide a semi-constrained mode of operation in which the fastener shaft is retained relative to the plate and the annular member is free to move within the fixation hole to change an angular orientation of the fastener shaft.

3. The bone fixation apparatus of claim 1, wherein the annular member has an expanded diameter sufficiently large to press against the fixation hole and arrest relative movement between the fixation hole and the fastener shaft in the expanded position.

4. The bone fixation apparatus of claim 1, wherein the expanded position includes a first expanded position permitting movement of the fastener shaft and annular member relative to the fixation hole and a second expanded position preventing movement of the fastener shaft and annular member relative to the fixation hole.

5. The bone fixation apparatus of claim 1, wherein the fastener shaft defines a circumferentially extending groove having a reduced diameter and the annular member is carried by the fastener shaft in the groove such that the annular member is coupled to the fastener shaft for relative articulation therewith.

6. The bone fixation apparatus of claim 1, wherein the annular member is selectively moved between the expanded position and the unexpanded position by rotation of the annular member relative to the fastener shaft.

7. The bone fixation apparatus of claim 1, wherein the C-shaped annular member includes a plurality of engagement formations spaced from the gap and operable to receive a tool to move the annular member between the expanded position and the unexpanded position by rotation of the annular member relative to the fastener shaft following insertion of the fastener shaft into a bone.

8. The bone fixation apparatus of claim 1, wherein the annular member comprises at least one engagement formation operable to receive a tool to move the annular member between the expanded position and the unexpanded position by rotation of the annular member relative to the fastener shaft using the tool.

9. A bone fixation apparatus comprising:
  a bone fixation plate having a fixation hole centered on a hole longitudinal axis with a curved inner surface that is longitudinally curved relative to the hole longitudinal axis;
  a fastener shaft having a longitudinal axis extending between a first end and a second end thereof along a shaft axis;
  a circumferential groove formed in the fastener shaft and having at least one circumferentially extending cam surface; and
  an annular member having an inner surface and a curved outer surface that is longitudinally curved relative to the hole longitudinal axis that is shaped to mate with the longitudinally curved inner surface, the inner surface cooperating with the at least one cam surface to radially expand the annular member from an unexpanded position to an expanded position when the fastener shaft is in a fixed position relative to the bone fixation plate, the annular member including separated ends defining a gap therebetween, the gap formed through the entire annular member;
  wherein the curved outer surface and the curved inner surface engage to allow orientation of the shaft axis of the fastener shaft at various angles relative to the hole longitudinal axis of the fixation hole of the bone fixation plate.

10. The bone fixation apparatus of claim 9, wherein the annular member has an expanded diameter sufficiently large to press against the fixation hole and arrest relative movement between the fixation hole and the fastener shaft in the expanded position, wherein the circumferentially extending groove carries the annular member such that the annular member is coupled to the fastener shaft for relative articulation therewith.

11. The bone fixation apparatus of claim 9, wherein the expanded position includes a first expanded position permitting movement of the fastener shaft and annular member relative to the fixation hole and a second expanded position preventing movement of the fastener shaft and annular member relative to the fixation hole.

12. The bone fixation apparatus of claim 9, wherein the fixation plate is a spinal fixation plate for securing first and second vertebral bodies relative to one another.

13. The bone fixation apparatus of claim 9, wherein the annular member is selectively moved between the expanded position and the unexpanded position by rotation of the annular member relative to the fastener shaft.

14. The bone fixation apparatus of claim 9, wherein the curved inner surface of the bone fixation plate extends from an upper surface of the bone fixation plate to a lower surface of the bone fixation plate.

15. A bone fixation apparatus comprising:
  a bone fixation plate having a spherical fixation hole with a curved inner surface;
  a fastener shaft having a longitudinal axis extending between a first end and a second end thereof;
  a circumferential groove formed in the fastener shaft and having at least one cam surface; and
  an annular member having an inner surface cooperating with the at least one cam surface to selectively expand the annular member from an unexpanded position to an expanded position independent of movement of the fastener shaft relative to the bone fixation plate and a curved outer surface conforming to the curved inner surface of the spherical fixation hole, the annular member including separated ends defining a gap therebetween, the gap formed through the entire annular member;
  wherein the fastener shaft can angularly articulate in the spherical fixation hole via engagement of the curved outer surface of the annular member with the curved inner surface of the spherical fixation hole when the annular member is in a first expanded position.

16. The bone fixation apparatus of claim 15, wherein the inner surface of the annular member and the at least one cam surface of the circumferential groove are cooperatively configured to provide a semi-constrained mode of operation in which the fastener shaft is retained relative to the plate and the annular member is free to move within the spherical fixation hole and a constrained mode of operation in which the fastener shaft is retained relative to the plate and the annular member is fixed in the spherical fixation hole.

17. The bone fixation apparatus of claim 15, wherein the annular member has an expanded diameter sufficiently large to press against the spherical fixation hole and arrest relative movement between the spherical fixation hole and the fastener shaft in the expanded position.

18. The bone fixation apparatus of claim 15, wherein the expanded position includes the first expanded position permitting movement of the fastener shaft and annular member relative to the spherical fixation hole and a second expanded position preventing movement of the fastener shaft and annular member relative to the spherical fixation hole.

19. The bone fixation apparatus of claim 15, wherein the circumferentially extending groove carries the annular member such that the annular member is coupled to the fastener shaft for relative articulation therewith.

20. The bone fixation apparatus of claim 15, wherein the annular member is selectively moved between the expanded position and the unexpanded position by rotation of the annular member relative to the fastener shaft.

* * * * *

UNITED STATES PATENT AND TRADEMARK OFFICE
CERTIFICATE OF CORRECTION

PATENT NO. : 10,010,357 B2
APPLICATION NO. : 14/254198
DATED : July 3, 2018
INVENTOR(S) : Ziolo et al.

Page 1 of 1

It is certified that error appears in the above-identified patent and that said Letters Patent is hereby corrected as shown below:

In the Claims

In Column 8, Line 11, in Claim 15, before "curved", insert --longitudinally--

In Column 8, Line 22, in Claim 15, before "curved", insert --longitudinally--

In Column 8, Line 28, in Claim 15, before "curved", insert --longitudinally--

In Column 8, Line 29, in Claim 15, before "curved", insert --longitudinally--

Signed and Sealed this
Eleventh Day of June, 2019

Andrei Iancu
*Director of the United States Patent and Trademark Office*